United States Patent
Cheng et al.

(10) Patent No.: US 9,580,422 B2
(45) Date of Patent: Feb. 28, 2017

(54) ISOTOPICALLY LABELED TRIAZOLOPYRIDINE 11-BETA HYDROXYSTEROID DEHYDROGENASE TYPE I INHIBITORS

(71) Applicant: BRISTOL-MYERS SQUIBB COMPANY, Princeton, NJ (US)

(72) Inventors: Yaofeng Cheng, Plainsboro, NJ (US); Weiqi Chen, Princeton, NJ (US); Brad D. Maxwell, Doylestown, PA (US); Bach D. Tran, Lawrenceville, NJ (US); Jun Li, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/031,301

(22) PCT Filed: Oct. 21, 2014

(86) PCT No.: PCT/US2014/061509
§ 371 (c)(1),
(2) Date: Apr. 22, 2016

(87) PCT Pub. No.: WO2015/061272
PCT Pub. Date: Apr. 30, 2015

(65) Prior Publication Data
US 2016/0257680 A1 Sep. 8, 2016

Related U.S. Application Data

(60) Provisional application No. 61/893,991, filed on Oct. 22, 2013.

(51) Int. Cl.
*A61K 31/44* (2006.01)
*C07D 401/00* (2006.01)
*C07D 471/04* (2006.01)
*C07B 59/00* (2006.01)
*A61K 31/437* (2006.01)

(52) U.S. Cl.
CPC .......... *C07D 471/04* (2013.01); *A61K 31/437* (2013.01); *C07B 59/002* (2013.01); *C07B 2200/05* (2013.01)

(58) Field of Classification Search
CPC .......................... C07D 249/08; C07D 471/04
USPC ........................ 514/300; 546/272.4
See application file for complete search history.

(56) References Cited

U.S. PATENT DOCUMENTS

| | | | |
|---|---|---|---|
| 7,718,669 B2 * | 5/2010 | Petry | C07D 487/04 514/300 |
| 8,486,964 B2 * | 7/2013 | Valeur | C07D 471/04 514/300 |
| 8,637,542 B2 * | 1/2014 | Liu | C07D 519/00 514/299 |
| 8,828,998 B2 * | 9/2014 | Palombella | 424/133.1 |

FOREIGN PATENT DOCUMENTS

WO    WO 2009/045753    4/2009

OTHER PUBLICATIONS

Foster, et al., Advances in Drug Research, vol. 14, pp. 1-40 (1985).
Tung, et al., Innovations in Pharmaceutical Technology, No. 32, pp. 24-26, Mar. 2010.

* cited by examiner

*Primary Examiner* — Raymond Henley, III
(74) *Attorney, Agent, or Firm* — Elliott Korsen

(57) ABSTRACT

Novel compounds are provided which are 11-beta-hydroxysteroid dehydrogenase type I inhibitors. 11-beta-hydroxysteroid dehydrogenase type I inhibitors are useful in treating, preventing, or slowing the progression of diseases requiring 11-beta-hydroxysteroid dehydrogenase type I inhibitor therapy. These novel compounds of formula I: or stereoisomers or pharmaceutically acceptable salts thereof, wherein R* is an isotopically labeled hydroxypropyl moiety.

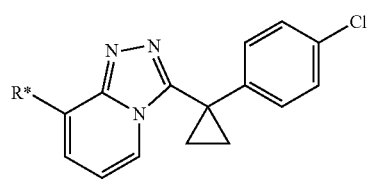

15 Claims, No Drawings

ISOTOPICALLY LABELED TRIAZOLOPYRIDINE 11-BETA HYDROXYSTEROID DEHYDROGENASE TYPE I INHIBITORS

CROSS-REFERENCES TO RELATED APPLICATION

This application claims priority benefit under Title 35 §119(e) of U.S. provisional Application 61/893,991 filed Oct. 22, 2013, the contents of which are herein incorporated by reference in its entirety.

BACKGROUND OF THE INVENTION

The steroid hormone cortisol is a key regulator of many physiological processes. However, an excess of cortisol, as occurs in Cushing's Disease, provokes severe metabolic abnormalities including: type 2 diabetes, cardiovascular disease, obesity, and osteoporosis. Many patients with these diseases, however, do not show significant increases in plasma cortisol levels. In addition to plasma cortisol, individual tissues can regulate their glucocorticoid tone via the in situ conversion of inactive cortisone to the active hormone cortisol. Indeed, the normally high plasma concentration of cortisone provides a ready supply of precursor for conversion to cortisol via the intracellular enzyme 11-beta-hydroxysteroid dehydrogenase type I (11beta-HSD1).

11beta-HSD1 is a member of the short chain dehydrogenase superfamily of enzymes. By catalyzing the conversion of cortisone to cortisol, 11beta-HSD1 controls the intracellular glucocorticoid tone according to its expression and activity levels. In this manner, 11beta-HSD1 can determine the overall metabolic status of the organ. 11beta-HSD1 is expressed at high levels in the liver and at lower levels in many metabolically active tissues including the adipose, the CNS, the pancreas, and the pituitary. Taking the example of the liver, it is predicted that high levels of 11beta-HSD1 activity will stimulate gluconeogenesis and overall glucose output. Conversely, reduction of 11beta-HSD1 activity will down regulate gluconeogenesis resulting in lower plasma glucose levels.

Various studies have been conducted that support this hypothesis. For example, transgenic mice expressing 2× the normal level of 11beta-HSD1 in only the adipose tissue show abdominal obesity, hyperglycemia, and insulin resistance. (Masuzaki, H. et al., "A Transgenic Model of Visceral Obesity and the Metabolic Syndrome", *Science*, 294:2166-2170 (2001). Conversely, when the 11beta-HSD1 gene is ablated by homologous recombination, the resulting mice are resistant to diet induced obesity and the accompanying dysregulation of glucose metabolism (Morton, N. M. et al., "Novel Adipose Tissue-Mediated Resistance to Diet-induced Visceral Obesity in 11β-Hydroxysteroid Dehydrogenase Type 1-Deficient Mice", *Diabetes*, 53:931-938 (2004). In addition, treatment of genetic mouse models of obesity and diabetes (ob/ob, db/db and KKAy mice) with a specific inhibitor of 11beta-HSD1 causes a decrease in glucose output from the liver and an overall increase in insulin sensitivity (Alberts, P. et al., "Selective Inhibition of 11β-Hydroxysteroid Dehydrogenase Type I Improves Hepatic Insulting Sensitivity in Hyperglycemic Mice Strains", *Endocrinology*, 144:4755-4762 (2003)). Furthermore, inhibitors of 11beta-HSD1 have been shown to be effective in treating metabolic syndrome and atherosclerosis in high fat fed mice (Hermanowski-Vosatka et al., *J. Exp. Med.*, 202(4):517-527 (2002)). Based in part on these studies, it is believed that local control of cortisol levels is important in metabolic diseases in these model systems. In addition, the results of these studies also suggest that inhibition of 11beta-HSD1 will be a viable strategy for treating metabolic diseases such as type 2 diabetes, obesity, and the metabolic syndrome.

Lending further support to this idea are the results of a series of preliminary clinical studies. For example, several reports have shown that adipose tissue from obese individuals has elevated levels of 11beta-HSD1 activity. In addition, studies with carbenoxolone, a natural product derived from licorice that inhibits both 11beta-HSD1 and 11beta-HSD2 (converts cortisol to cortisone in kidney) have shown promising results. A seven day, double blind, placebo controlled, cross over study with carbenoxolone in mildly overweight individuals with type 2 diabetes showed that patients treated with the inhibitor, but not the placebo group, displayed a decrease in hepatic glucose production (Andrews, R. C. et al., *J. Clin. Endocrinol. Metab.*, 88:285-291 (2003)). This observation is consistent with the inhibition of 11beta-HSD1 in the liver. The results of these preclinical and early clinical studies strongly support the concept that treatment with a potent and selective inhibitor of 11beta-HSD1 will be an efficacious therapy in patients afflicted with type 2 diabetes, obesity, and the metabolic syndrome.

Accordingly, compounds that activate 11beta-HSD1 could demonstrate a wide range of utilities in treating diabetes and related conditions, microvascular complications associated with diabetes, the macrovascular complications associated with diabetes, cardiovascular diseases, Metabolic Syndrome and its component conditions, inflammatory diseases and other maladies. PCT Publication Nos. WO 2006/135667 A1, WO 2006/135795 A1, WO 2008/024892 A1, WO 2008/130951 A1, WO 2009/045753 A1 (incorporated herein by reference and assigned to present applicant) and WO 2009/102761 A1, disclose compounds that activate 11beta-HSD1. The references also disclose various processes to prepare these compounds.

It is desirable to find new compounds with improved pharmacological characteristics compared with known 11beta-HSD1 activators. For example, it is desirable to find new compounds with improved 11beta-HSD1 activity and selectivity for 11beta-HSD1 versus other dehydrogenase receptors (i.e., 11beta-HSD2 receptor). It is also desirable to find compounds with advantageous and improved characteristics in one or more of the following categories:

(a) pharmaceutical properties (i.e., solubility, permeability, amenability to sustained release formulations);

(b) dosage requirements (e.g., lower dosages and/or once-daily dosing);

(c) factors which decrease blood concentration peak-to-trough characteristics (i.e., clearance and/or volume of distribution);

(d) factors that increase the concentration of active drug at the receptor (i.e., protein binding, volume of distribution);

(e) factors that decrease the liability for clinical drug-drug interactions (cytochrome P450 enzyme inhibition or induction, such as CYP 2D6 inhibition, see Dresser, G. K. et al., *Clin. Pharmacokinet.*, 38:41-57 (2000), which is hereby incorporated by reference); and (f) factors that decrease the potential for adverse side-effects (e.g., pharmacological selectivity beyond the intracellular enzyme 11-beta-hydroxysteroid dehydrogenase type I, potential chemical or metabolic reactivity, limited CNS penetration, ion-channel selectivity). It is especially desir-

3 able to find compounds having a desirable combination of the aforementioned pharmacological characteristics.

SUMMARY OF THE INVENTION

The present invention relates to isotopically-labeled compounds, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S.

In accordance with the present invention, bicyclic and related compounds, enantiomers, diastereomers, tautomers, prodrugs, solvates or salts thereof, are provided that have the general structure of formula I:

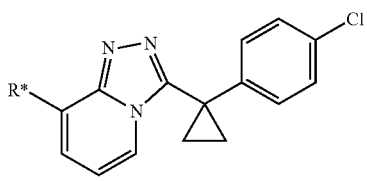

I wherein R* is an isotopically labeled hydroxypropyl moiety.

The compounds of the present invention are believed to inhibit the activity of the enzyme 11-beta-hydroxysteroid dehydrogenase type I. Consequently, the compounds of the present invention may be used in the treatment of multiple diseases or disorders associated with 11-beta-hydroxysteroid dehydrogenase type I, such as diabetes and related conditions, microvascular complications associated with diabetes, the macrovascular complications associated with diabetes, cardiovascular diseases, Metabolic Syndrome and its component conditions, inflammatory diseases and other maladies. Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequalae (acute coronary syndrome, myocardial infarction, angina pectoris, peripheral vascular disease, intermittent claudication), abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma and inflammatory diseases, such as, rheumatoid arthritis, Cushing's Disease, Alzheimer's Disease and osteoarthritis.

The present invention provides for compounds of formula I or II, pharmaceutical compositions employing such compounds, and for methods of using such compounds. In particular, the present invention provides a pharmaceutical composition comprising a therapeutically effective amount of a compound of formula I or II alone or in combination with a pharmaceutically acceptable carrier.

Further, in accordance with the present invention, a method is provided for preventing, inhibiting, or treating the progression or onset of diseases or disorders associated with the activity of the enzyme 11-beta-hydroxysteroid dehydrogenase type I, such as defined above and hereinafter, wherein a therapeutically effective amount of a compound of formula I or II is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting, or treating the diseases as defined above and hereinafter, wherein a therapeutically effective amount of a combination of a compound of formula I or II and another compound of formula I or II and/or at least one other type of therapeutic agent, is administered to a mammalian, i.e., human, patient in need of treatment.

The present invention also describes compounds that are believed to have a beneficial improvement in metabolic stability, in particular, metabolic stability in human liver microsomes, in comparison to compounds previously disclosed in the art, such as those disclosed in PCT Publication No. WO 2009/045753 A1.

Additionally, compounds of the present invention are believed to have a beneficial, preferably a two-fold, more preferably, a three-fold, decrease in liability for clinical drug-drug interactions (cytochrome P450 enzyme inhibition or induction, such as CYP 2C19 inhibition) in comparison to compounds previously disclosed in the art, such as those disclosed in PCT Publication No. WO 2009/045753 A1.

Furthermore, compounds of the present invention are believed to show unexpected advantages over compounds previously disclosed in the art, such as those disclosed in PCT Publication No. WO 2009/045753 A1. The present compounds are believed to have a desirable combination of decreased liability for clinical drug-drug interactions (cytochrome P450 enzyme inhibition or induction, such as CYP 2C19 inhibition) and metabolic stability in a human liver microsomal assay without a loss in pharmacological activity. Such compounds should be more useful in the treatment, inhibition or amelioration of one or more diseases or disorders that are discussed herein.

DESCRIPTION OF THE INVENTION

In accordance with the present invention, compounds of formula I

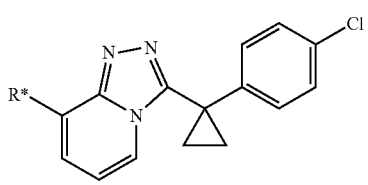

I or enantiomers, diastereomers, tautomers, prodrugs, solvates or salts thereof wherein wherein R* is an isotopically labeled hydroxypropyl moiety.

In yet another embodiment, the present invention provides compounds, enantiomers, diastereomers, tautomers, prodrugs, solvates or salts thereof, wherein the compounds are compounds of formula Ia, Ib, Ic, Id, Ie, If or Ig:

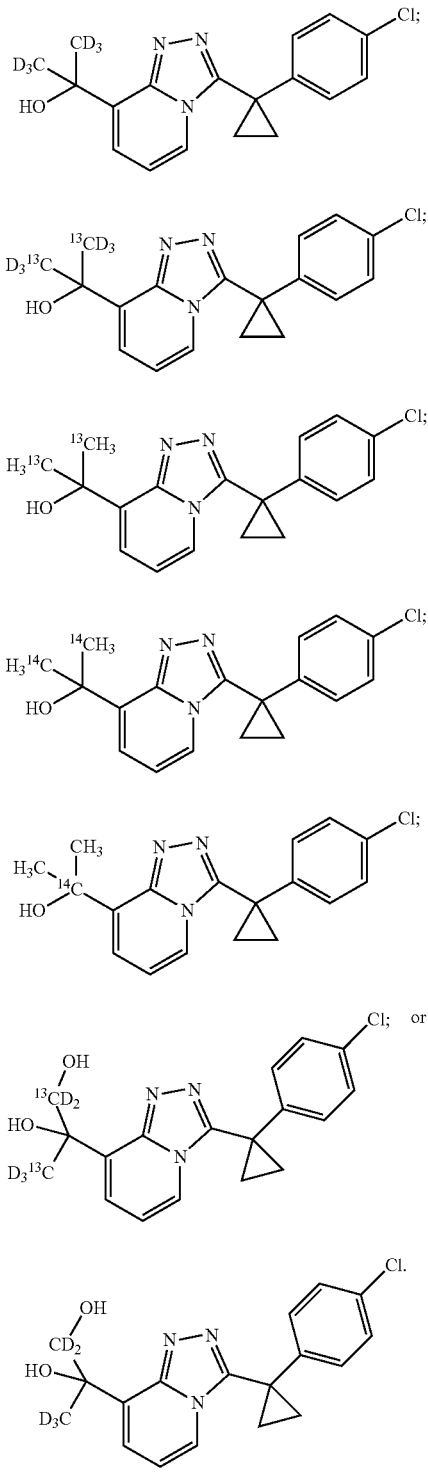

In another embodiment, the present invention provides compounds, enantiomers, diastereomers, tautomers, prodrugs, solvates or salts thereof, wherein the compounds are compounds of Formula Ia or Ib.

In another embodiment, the present invention provides compounds, enantiomers, diastereomers, tautomers, prodrugs, solvates or salts thereof, wherein the compounds are compounds of Formula Ia.

In another embodiment, the present invention provides compounds, enantiomers, diastereomers, tautomers, prodrugs, solvates or salts thereof, wherein the compounds are compounds of Formula Ib.

In another embodiment, the present invention provides compounds, enantiomers, diastereomers, tautomers, prodrugs, solvates or salts thereof, wherein the compounds are compounds of Formula Ic.

In another embodiment, the present invention provides compounds, enantiomers, diastereomers, tautomers, prodrugs, solvates or salts thereof, wherein the compounds are compounds of Formula Id.

In another embodiment, the present invention provides compounds, enantiomers, diastereomers, tautomers, prodrugs, solvates or salts thereof, wherein the compounds are compounds of Formula Ie.

In another embodiment, the present invention provides compounds, enantiomers, diastereomers, tautomers, prodrugs, solvates or salts thereof, wherein the compounds are compounds of Formula If.

In another embodiment, the present invention provides compounds, enantiomers, diastereomers, tautomers, prodrugs, solvates or salts thereof, wherein the compounds are compounds of Formula Ig.

In one embodiment, the present invention provides compounds, enantiomers, diastereomers, tautomers, prodrugs, solvates or salts thereof, wherein the compounds are compounds of Formula II:

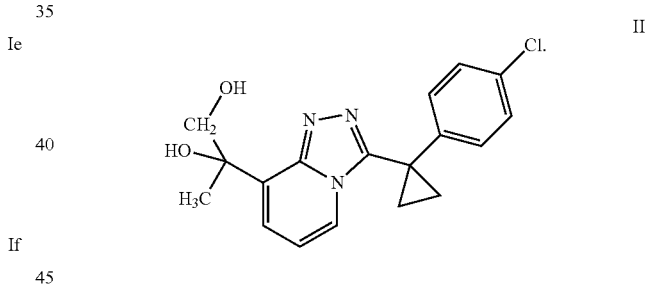

In another embodiment, the present invention relates to pharmaceutical compositions comprised of a therapeutically effective amount of a compound of formula I, Ia, Ib, Ic, Id, Ie, If, Ig or II, alone or, optionally, in combination with a pharmaceutically acceptable carrier and/or one or more other agent(s).

In another embodiment, the present invention relates to methods of inhibiting the activity of the enzyme 11-beta-hydroxysteroid dehydrogenase type I comprising administering to a mammalian patient, for example, a human patient, in need thereof a therapeutically effective amount of a compound of formula I, Ia, Ib, Ic, Id, Ie, If, Ig or II, alone, or optionally, in combination with another compound of a compound of formula I, Ia, Ib, Ic, Id, Ie, If, Ig or II and/or at least one other type of therapeutic agent.

In another embodiment, the present invention relates to a method for preventing, inhibiting, or treating the progression or onset of diseases or disorders associated with the activity of the enzyme 11-beta-hydroxysteroid dehydrogenase type I comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

Examples of diseases or disorders associated with the activity of the enzyme 11-beta-hydroxysteroid dehydrogenase type I that can be prevented, inhibited, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis, acute coronary syndrome, myocardial infarction, angina pectoris, peripheral vascular disease, intermittent claudication, abnormal heart function, myocardial ischemia, stroke, Metabolic Syndrome, hypertension, obesity, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy, glaucoma, rheumatoid arthritis, Cushing's Disease, Alzheimer's Disease and osteoarthritis.

In another embodiment, the present invention relates to a method for preventing, inhibiting, or treating the progression or onset of diabetes, hyperglycemia, obesity, dyslipidemia, hypertension, cognitive impairment, rheumatoid arthritis, osteoarthritis, glaucoma, Cushing's Disease and Metabolic Syndrome comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In still another embodiment, the present invention relates to a method for preventing, inhibiting, or treating the progression or onset of diabetes, comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In yet still another embodiment, the present invention relates to a method for preventing, inhibiting, or treating the progression or onset of hyperglycemia comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of obesity comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In one embodiment, the present invention relates to a method for preventing, inhibiting, or treating the progression or onset of dyslipidemia comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of hypertension comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of cognitive impairment comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of rheumatoid arthritis comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of osteoarthritis comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of Metabolic Syndrome comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of glaucoma comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

In another embodiment, the present invention relates to a method for preventing, inhibiting, or treating the progression or onset of Cushing's Disease comprising administering to a mammalian patient, for example, a human patient, in need of prevention, inhibition, or treatment a therapeutically effective amount of a compound of formula I, Ia, Ib, Ic, Id, Ie, If, Ig or II, alone, or, optionally, in combination with another compound of formula I, Ia, Ib, Ic, Id, Ie, If, Ig or II and/or at least one other type of therapeutic agent.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of the present invention may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Young, S. D. et al., *Antimicrobial Agents and Chemotherapy*, 2602-2605 (1995).

To the extent that compounds of the present invention, and salts thereof, may exist in their tautomeric form, all such tautomeric forms are contemplated herein as part of the present invention.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, bisulfate and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., the compound of formula I or II) is a prodrug within the scope and spirit of the invention.

The term "prodrugs" as employed herein includes esters and carbonates formed by reacting one or more hydroxyls of compounds of the present invention with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds., Ch. 5, pp. 113-191 (Harwood Academic Publishers, 1991); and d) *Hydrolysis in Drug and Prodrug Metabolism*, Bernard Testa and Joachim M. Mayer (Wiley-VCH, 2003).

Said references are incorporated herein by reference.

In addition, compounds of the present invention are, subsequent to their preparation, preferably isolated and purified to obtain a composition containing an amount by weight equal to or greater than 99% formula I or II compound ("substantially pure" compound I or II), which is then used or formulated as described herein. Such "substantially pure" compounds of the formula I or II are also contemplated herein as part of the present invention.

All stereoisomers of the compounds of the instant invention are contemplated, either in admixture or in pure or substantially pure form. The compounds of the present invention can have asymmetric centers at any of the carbon atoms and/or exhibit polymorphism. Consequently, compounds of the present invention can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization. In addition, the compounds of present invention may exist in tautomeric form. Such tautomeric forms of the formula I or II are also contemplated herein as part of the present invention.

"Stable compound" and "stable structure" are meant to indicate a compound that is sufficiently robust to survive isolation, handling and storage to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit the activity of the enzyme 11-beta-hydroxysteroid dehydrogenase type I or effective to treat or prevent metabolic or other disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being affected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

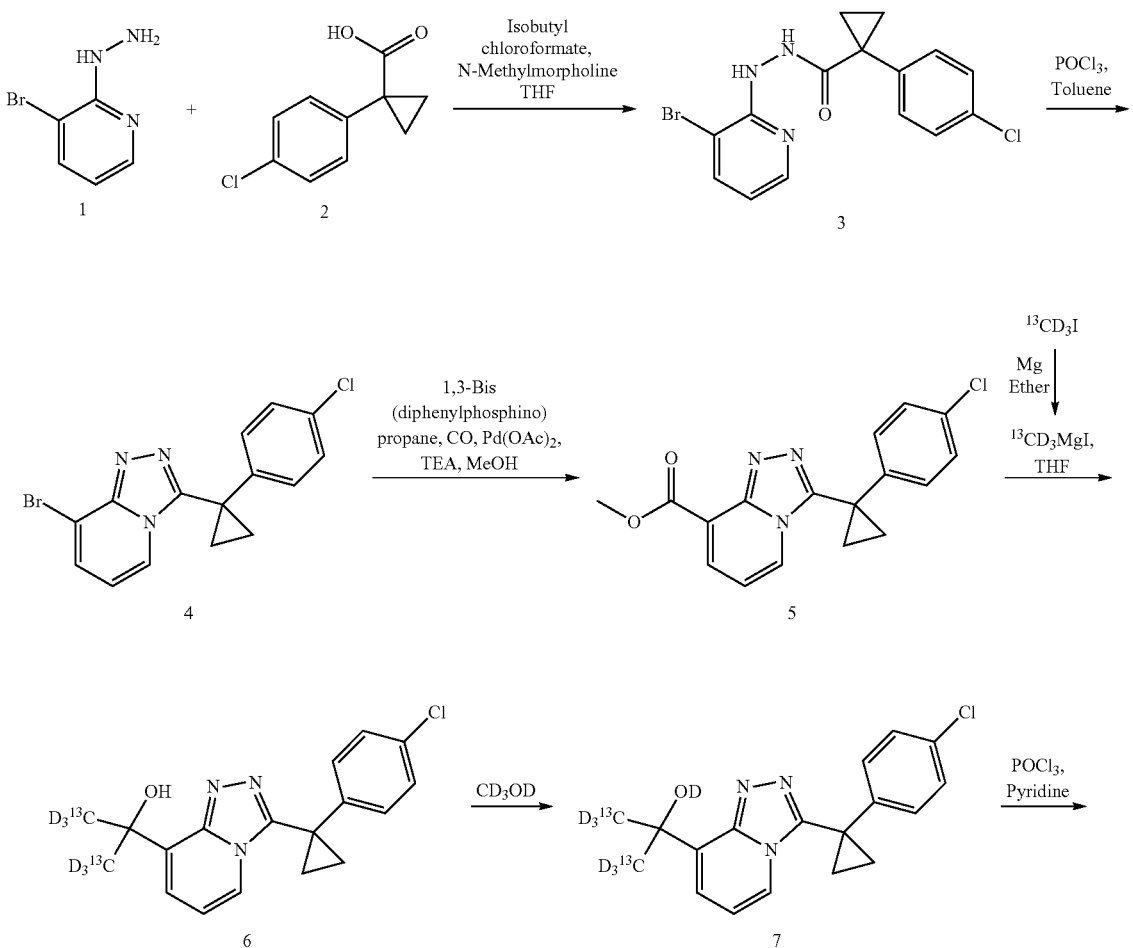

Scheme 1

13  14
-continued
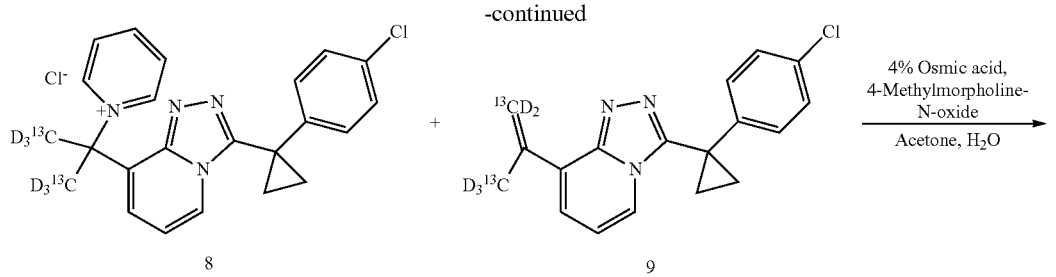
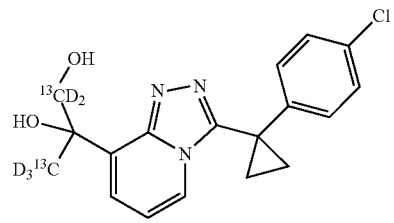
10
Scheme 2
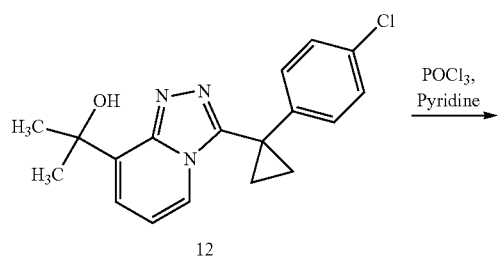
12
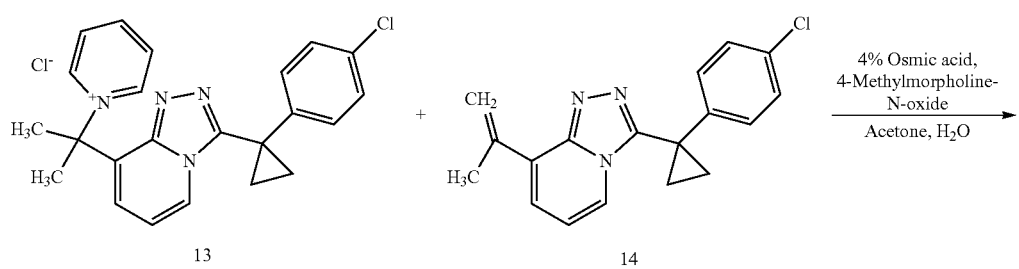
13  14
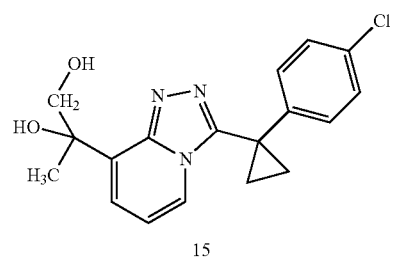
15

Scheme 3

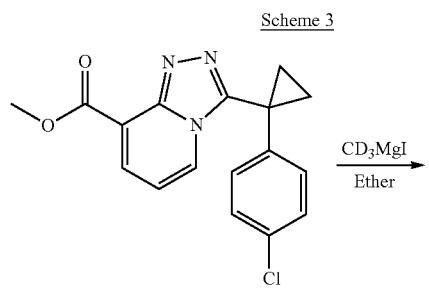

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using the same.

As appropriate, reactions were conducted under an atmosphere of dry nitrogen (or argon). For anhydrous reactions, DRISOLV® solvents from EM or anhydrous solvents from Sigma-Aldrich were employed. For other reactions, reagent grade or HPLC grade solvents were utilized. Unless otherwise stated, all commercially obtained reagents were used as received.

LC/MS measurements were obtained using a Shimadzu HPLC/Waters ZQ single quadrupole mass spectrometer hybrid system or a Finnigan LXQ LC/MS System. Data for the peak of interest are reported from positive-mode electrospray ionization. NMR (nuclear magnetic resonance) spectra were typically obtained on Bruker or JEOL 300 MHz, 400 MHz and 500 MHz instruments in the indicated solvents. All chemical shifts are reported in ppm from tetramethylsilane with the solvent resonance as the internal standard. $^1$H-NMR spectral data are typically reported as follows: chemical shift, multiplicity (s=singlet, br s=broad singlet, d=doublet, dd=doublet of doublets, t=triplet, q=quartet, sep=septet, m=multiplet, app=apparent), coupling constants (Hz), and integration.

One of skill in the art will recognize the standard abbreviations utilized herein, throughout the specification. For ease of reference, the abbreviations include, but are not necessarily limited to: sat.=saturated, HPLC=high-performance liquid chromatography, AP=area percent, KF=Karl-Fischer, RT=room temperature, mmol=millimoles, MS=mass spectroscopy, CDCl$_3$=deuterated chloroform, CD$_3$OD=deuterated methanol, NMP=N-methylpyrrolidone, TEA=triethylamine, DIPEA=Diisopropylethylamine, IPA=isopropyl alcohol, TFA=trifluoroacetic acid, HCl=hydrochloric acid, EtOAc=ethyl acetate, CH$_2$Cl$_2$=methylene chloride, THF=tetrahydrofuran, DMF=N,N-dimethylformamide, SiO$_2$=silicon dioxide, NaOH=sodium hydroxide, DMSO=dimethylsulfoxide, ° C.=degrees Celsius, g=gram or grams, mg=milligram or milligrams, mm=millimeter, mL (or ml)=milliliter or milliliters, h=hour or hours, M=molar, N=normal, min=minute or minutes, MHz=megahertz, tlc=thin layer chromatography, v/v=volume to volume ratio, v/v/v=volume to volume to volume ratio and ca.=about.

"α", "β", "R" and "S" are stereochemical designations familiar to those skilled in the art.

Example 1

N'-(3-Bromopyridin-2-yl)-1-(4-chlorophenyl)cyclopropanecarbohydrazide

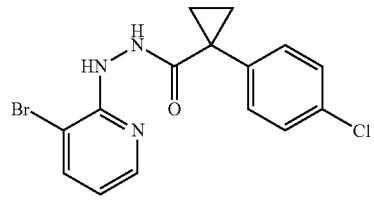 [SMILES: O=C(NNc1ncccc1Br)C1(c2ccc(Cl)cc2)CC1]

A mixture of 1-(4-chlorophenyl)cyclopropanecarboxylic acid (2.650 g, 13.48 mmol) and N-methylmorpholine (2.65 ml, 24.12 mmol) in 106 mL of THF was cooled to 0° C. To this was added isobutyl chloroformate (2.212 ml, 16.85 mmol) dropwise over a period of 10 min. The mixture was allowed to stir at 0° C. for 1 h, and then a solution of 3-bromo-2-hydrazinylpyridine (3.17 g, 16.85 mmol) in 20 mL of THF was added. The reaction mixture was warmed to RT and stirred for 16 h. TLC analysis on silica gel using 5/95 (v/v) MeOH/CH$_2$Cl$_2$ and LC/MS analysis showed the reaction to be completed. The reaction was quenched with water. The organic layer was separated and the aqueous layer was extracted with EtOAc. The combined organic extracts were dried over anhydrous MgSO$_4$, filtered and concentrated in vacuo to give a light brown solid. This solid was triturated with 1/1 (v/v) ether/hexane (2×4 mL) to remove some of the light brown color. The solvents were decanted and the resulting solid was dried under vacuum to give 4.5 g (82% yield) of a light yellow white solid. $^1$H-NMR (DMSO-d$_6$, 400 MHz) δ 9.09 (d, J=2.0 Hz, 1H), 8.09 (dd, J=4.8, 1.5 Hz, 1H), 8.04 (d, J=2.0 Hz, 1H), 7.85-7.79 (m, 1H), 7.49-7.44 (m, 2H), 7.42-7.38 (m, 2H), 6.68 (dd, J=7.6, 4.7 Hz, 1H), 1.45-1.38 (m, 2H), 1.11-1.05 (m, 2H). LC/MS (ESI) 366.0/368.0/370.0 (M+1/M+3/M+5). The product was used with no further purification in the next step.

Example 2

8-Bromo-3-(1-(4-chlorophenyl)cyclopropyl)-[1,2,4]triazolo[4,3-a]pyridine

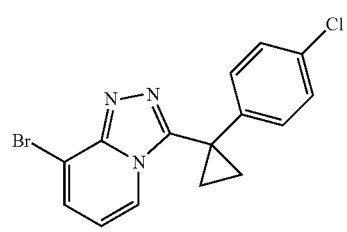 [SMILES: Clc1ccc(C2(c3nnc4c(Br)cccn34)CC2)cc1]

To N'-(3-bromopyridin-2-yl)-1-(4-chlorophenyl)cyclopropanecarbohydrazide (4.5 g, 12.27 mmol) in toluene (100 mL) was added POCl$_3$ (9.12 mL, 98.2 mmol). The yellow solution was refluxed for 2 h. LC/MS analysis showed the presence of starting material still remained. The solution was refluxed for an additional 16 h which became a suspension. The suspension was cooled to 0° C. and poured into cold 1 N NaOH. Solid KOH was added till the pH was 8-9. The aqueous layer was extracted with EtOAc. The combined organic extracts were washed with water, brine and dried over Na$_2$CO$_3$. After filtration and concentration in vacuo, a white solid was obtained. The white solid was triturated with 1/1 (v/v) ether/hexane (2×10 mL). The solvents were decanted and the resulting solid was dried under vacuum to give 1.85 g (41.1% yield of white solid, 8-bromo-3-(1-(4-chlorophenyl)cyclopropyl)-[1,2,4]triazolo[4,3-a]pyridine, $^1$H NMR (CD$_3$OD, 500 MHz) δ 8.19 (dd, J=6.9, 0.8 Hz, 1H), 7.75 (dd, J=7.2, 0.8 Hz, 1H), 7.33-7.27 (m, 2H), 7.17-7.12 (m, 2H), 6.89 (t, J=7.1 Hz, 1H), 1.72-1.67 (m, 2H), 1.66-1.62 (m, 2H). LC/MS (ESI) 348.0/350.0/352.0 (M+1/M+3/M+5).

Example 3

Methyl 3-(1-(4-chlorophenyl)cyclopropyl)-[1,2,4]triazolo[4,3-a]pyridine-8-carboxylate

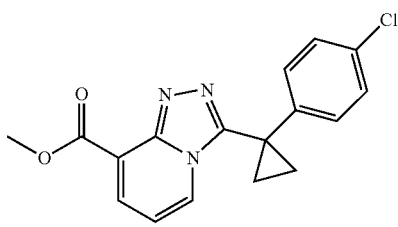 [SMILES: COC(=O)c1cccn2c(C3(c4ccc(Cl)cc4)CC3)nnc12]

Using a pressure reactor manifold apparatus and a 75 mL glass pressure vessel, a mixture of 8-bromo-3-(1-(4-chlorophenyl)cyclopropyl)-[1,2,4]triazolo[4,3-a]pyridine (1.00 g, 2.87 mmol), palladium (II) acetate (0.064 g, 0.287 mmol), 1,3-bis(diphenylphosphino)propane (0.118 g, 0.287 mmol) and triethylamine (1.199 ml, 8.61 mmol) in MeOH (28.7 ml) with stirring under nitrogen was charged with approximately 25 psi CO (g). The reaction mixture was subjected to four freeze, pump, thaw cycles using a dry ice acetone bath and then pressurized with CO (g) to 25 psi. The mixture was heated to 50° C. with stirring overnight. The reaction mixture was cooled to RT and the system subjected to two freeze, pump, and thaw cycles to remove unreacted CO (g). HPLC and LC/MS analysis indicated the reaction was completed. TLC analysis on silica gel using 12.5/37.5/50.0 (v/v/v) MeOH/EtOAc/Hexane showed negligible starting material left. The crude reaction solution was combined with that of the same from another reaction and the solvent was removed in vacuo to obtain a dark brown/black viscous oil. The crude product was dissolved in CH$_2$Cl$_2$ (60 mL) and stirred with 50% sat. aqueous ammonium chloride (20 mL) for 30 min. The layers were separated and the CH$_2$Cl$_2$ was removed in vacuo to give 2.4956 g of the crude product. The crude product was purified by Flash Chromatography using a 120 g Isco silica gel column and eluting with a gradient from 5/15/80 (v/v/v) MeOH/EtOAc/hexane to 7.5/22.5/70 (v/v/v) MeOH/EtOAc/hexane and collecting 30 mL fractions. Fractions were analyzed by HPLC to determine which contained the desired product. Fractions 46 to 85 were pooled and the solvent removed in vacuo to give 1.6656 g (86% yield) of yellow foam. $^1$H NMR (CDCl$_3$, 300 MHz) δ 8.05 (dd, J=7.0, 1.2 Hz, 1H), 7.99 (dd, J=6.7, 1.2 Hz, 1H), 7.28-7.20 (m, 2H), 7.07-7.01 (m, 2H), 6.84 (t, J=6.9 Hz, 1H), 4.09 (s, 3H), 1.75-1.69 (m, 2H), 1.59-1.53 (m, 2H). LC/MS (ESI) 328.1/330.1 (M+1/M+3).

Example 4

[($^{13}$CD$_3$)$_2$]2-(3-(1-(4-chlorophenyl)cyclopropyl)-[1,2,4]triazolo[4,3-a]pyridin-8-yl)propan-2-ol

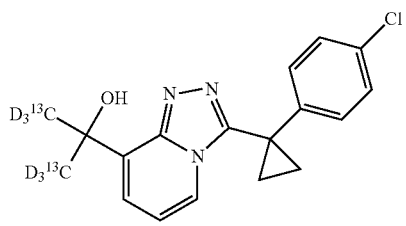

To an oven dried 50 ml round bottom flask with septum and stirbar was weighed magnesium (0.348 g, 14.33 mmol). To the flask was syringed anhydrous diethyl ether (10 mL). The reaction was cooled to 0° C. To the flask was slowly added [$^{13}$CD$_3$] iodomethane (0.894 ml, 14.33 mmol). The reaction was stirred at RT for 2 h. To a separate 100 mL oven dried flask containing methyl 3-(1-(4-chlorophenyl)cyclopropyl)-[1,2,4]triazolo[4,3-a]pyridine-8-carboxylate (1.5656 g, 4.78 mmol) dissolved in anhydrous THF (30.8 ml) at 0° C. was cannulated the newly generated Grignard reagent. Anhydrous diethyl ether (7.0 mL) was used to rinse the Grignard production flask and the rinsings were also cannulated into the flask containing the ester. The reaction mixture was warmed to RT. After 90 min, HPLC and LC/MS analysis showed the reaction to be mostly complete. The reaction was cooled to 0° C., brine (15.0 mL) was slowly added and the mixture was warmed to RT. The crude mixture was combined with that of the same from a reaction at approximately half the scale and the aqueous layer was extracted with EtOAc (5×50 mL). The combined organic extracts were washed with brine (10.0 mL) and the solvent was removed in vacuo. The crude product was purified by flash chromatography using a 24 g Isco silica gel column using a gradient from 35/65 (v/v) EtOAc/hexane to 50/50 (v/v) EtOAc/hexane. The fractions containing pure product were pooled and the solvent was removed in vacuo to give 1.1694 g (49% yield) of a pale yellow glass. $^1$H NMR (DMSO-d$_6$, 300 MHz) δ 8.07-7.99 (m, 1H), 7.42 (d, J=6.5 Hz, 1H), 7.37-7.30 (m, 2H), 7.14-7.06 (m, 2H), 6.94 (t, J=6.9 Hz, 1H), 1.65-1.51 (m, 4H). LC/MS (ESI) 336.3/338.3 (M+1/M+3).

Example 5

[(OD)($^{13}$CD$_3$)$_2$]2-(3-(1-(4-chlorophenyl)cyclopropyl)-[1,2,4]triazolo[4,3-a]pyridin-8-yl)propan-2-ol

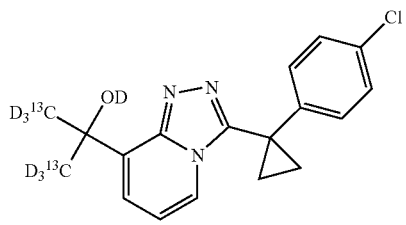

To a roundbottom flask was transferred [($^{13}$CD$_3$)$_2$]2-(3-(1-(4-chlorophenyl)cyclopropyl)-[1,2,4]triazolo[4,3-a]pyridin-8-yl)propan-2-ol (1.1694 g, 3.45 mmol) and that of the same from a small scale practice reaction (91.6 mg, 0.273 mmol). To the flask was added CD$_3$OD (10 mL). After dissolving the material completely, the solvent was removed in vacuo. The solid was dissolved again in CD$_3$OD (10 mL) and the solvent removed in vacuo to give 1.1872 g (94% yield) of a pale yellow glass. $^1$H NMR (DMSO-d$_6$, 300 MHz) δ 8.07-8.00 (m, 1H), 7.41 (d, J=6.7 Hz, 1H), 7.37-7.28 (m, 2H), 7.15-7.04 (m, 2H), 6.93 (t, J=6.9 Hz, 1H), 1.57 (d, J=5.0 Hz, 4H). LC/MS (ESI) 336.3/338.3 (M+1/M+3). The deuterium on the oxygen exchanged back to a proton in the mobile phase of the LC.

Example 6

[(CD$_3$)$_2$]2-(3-(1-(4-chlorophenyl)cyclopropyl)-[1,2,4]triazolo[4,3-a]pyridin-8-yl)propan-2-ol trifluoroacetic acid salt

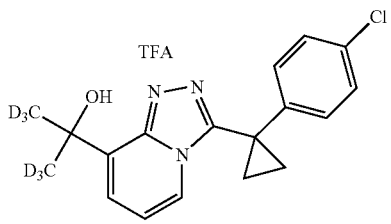 [SMILES: [2H]C([2H])([2H])C(O)(c1cccn2c(C3(c4ccc(Cl)cc4)CC3)nnc12)C([2H])([2H])[2H]]

To a dry two neck flask with a stirbar was weighed methyl 3-(1-(4-chlorophenyl)cyclopropyl)-[1,2,4]triazolo[4,3-a]pyridine-8-carboxylate (250.0 mg, 0.763 mmol). To this was syringed anhydrous diethyl ether (10.0 mL) and the mixture was stirred to dissolve the yellow solid. The flask was attached to a reflux condenser and methyl-D$_3$ magnesium iodide (1.678 mL, 1.678 mmol) in diethyl ether was added dropwise over 15 min. A solid formed upon the addition of the Grignard reagent and then slowly dissolved near the end of the addition of all of the solution. The reaction mixture was stirred at room temperature under nitrogen overnight. To the reaction was added methyl-D$_3$-magnesium iodide in diethyl ether (0.70 mL, 0.70 mmol) and the reaction was stirred at RT for an additional 2.5 h. The reaction mixture was cooled in an ice-water bath and 1M NH$_4$Cl (aq) (1.0 mL) was added dropwise over 15 min. The solution was warmed to RT and the layers were separated. The aqueous layer was extracted with EtOAc (6×10 mL). The combined organic extracts were washed with water (1×15 mL), brine (1×10 mL), dried over Na$_2$SO$_4$, filtered and the solvent was removed in vacuo to give a 150.3 mg of yellow brown oil. The crude product was dissolved in 2.0 mL of 0.1% TFA in acetonitrile and 1.0 mL of 0.1% TFA in water and was purified by semi-preparative HPLC on a Phenomenex LUNA C18, 21.1 mm×250 mm column. Solvent A=0.1% TFA in Water, Solvent B=0.1% TFA in acetonitrile, Gradient: 0 min 30% B, 20 min 80% B, Flowrate=20 ml/min, UV—254 nm, Injection volume=100 μl. The product with a retention time=7.9-8.0 min. was collected, pooled and the solvent removed in vacuo to give a 33.2 mg of a white solid. $^1$H NMR (DMSO-d$_6$, 400 MHz) δ 8.11 (d, J=6.8 Hz, 1H), 7.51 (d, J=6.6 Hz, 1H), 7.39-7.31 (m, 2H), 7.17-7.10 (m, 2H), 7.02 (t, J=6.8 Hz, 1H), 1.65-1.54 (m, 4H). $^{19}$F NMR (376.46 MHz, DMSO-d$_6$) δ 74.45, 74.50 75.18. LC/MS (ESI) 333/335 (M+1/M+3).

Example 7

3-(1-(4-Chlorophenyl)cyclopropyl)-8-(prop-1-en-2-yl)-[1,2,4]triazolo[4,3-a]pyridine and 1-(2-(3-(1-(4-chlorophenyl)cyclopropyl)-[1,2,4]triazolo[4,3-a]pyridin-8-yl)propan-2-yl)pyridin-1-ium chloride

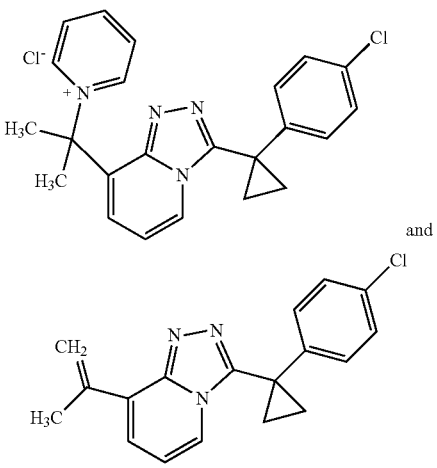

To a round bottom flask was weighed 2-(3-(1-(4-chlorophenyl)cyclopropyl)-[1,2,4]triazolo[4,3-a]pyridin-8-yl)propan-2-ol hydrochloride, (200 mg, 0.499 mmol). To this was added pyridine (0.764 ml) and the solution was cooled to 0° C. followed by the slow addition of phosphorus oxychloride (0.233 ml, 2.495 mmol) over 10 min with stirring. The mixture was stirred at 0° C. for 10 min and then heated to 60° C. for 2 h. The reaction mixture was cooled to RT and solvent removed in vacuo, chilled to 0° C., CH$_2$Cl$_2$ (4 ml) was added to the pasty white residue then H$_2$O (1.0 ml) was carefully added. To the solution was added solid sodium carbonate to adjust the pH to ~8 by pH paper. The aqueous layer was extracted with CH$_2$Cl$_2$ (5×4 ml), EtOAc (2×4 ml) and CH$_2$Cl$_2$ (2×4 ml). The combined organic extracts were concentrated in vacuo to give 241.5 mg of a viscous yellow liquid. The crude product was purified by Flash Chromatography using an Isco 4 g silica gel column, eluting with a gradient 0/100 (v/v) MeOH/CH$_2$Cl$_2$ to 3/97 (v/v) MeOH/CH$_2$Cl$_2$ and then with 10/90 (v/v) MeOH/CH$_2$Cl$_2$ to elute the more polar pyridine adduct. Fractions of 15 ml were collected. Fractions containing the alkene product were pooled and the solvent removed in vacuo to give 76.4 mg (49.4% yield) of an off-white solid. $^1$H NMR (DMSO-d$_6$, 300 MHz) δ 8.07 (dd, J=6.9, 0.7 Hz, 1H), 7.40-7.36 (m, 1H), 7.35-7.29 (m, 2H), 7.10-7.04 (m, 2H), 6.97 (t, J=6.9 Hz, 1H), 6.78 (d, J=2.1 Hz, 1H), 5.59 (s, 1H), 2.24 (d, J=0.6 Hz, 3H), 1.60 (d, J=3.2 Hz, 4H). LC/MS (ESI) 310.2/312.2. Fractions containing the pyridine adduct were combined and solvent removed in vacuo to give 122.2 mg of a viscous pale yellow oil. $^1$H NMR (DMSO-d$_6$, 300 MHz) δ 9.22 (d, J=5.9 Hz, 1H), 8.59 (t, J=7.8 Hz, 1H), 8.33-8.24 (m, 1H), 8.08 (t, J=7.2 Hz, 3H), 7.78-7.67 (m, 1H), 7.38-7.26 (m, 2H), 7.20-7.04 (m, 3H), 2.28 (s, 6H), 1.51 (d, J=6.5 Hz, 4H). LC/MS (ESI) 310.3/312.2 (M+1/M+3) was detected from the loss of pyridine to form the tertiary and benzylic carbocation.

21
Example 8

3-(1-(4-Chlorophenyl)cyclopropyl)-8-(prop-1-en-2-yl)-[1,2,4]triazolo[4,3-a]pyridine

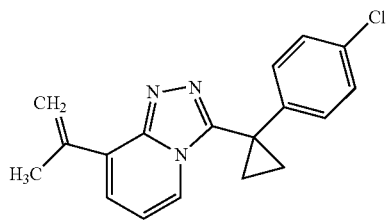 [SMILES: C=C(C)c1cccn2c(C3(c4ccc(Cl)cc4)CC3)nnc12]

To a 1 ml vial was weighed 1-(2-(3-(1-(4-chlorophenyl)cyclopropyl)-[1,2,4]triazolo[4,3-a]pyridin-8-yl)propan-2-yl)pyridin-1-ium chloride (15.7 mg, 0.040 mmol) in anhydrous toluene (0.403 ml) under nitrogen at RT. The reaction was stirred for 5 h at 100° C. and then cooled to RT overnight. The toluene was removed in vacuo to obtain 13.6 mg of a pale yellow solid. To the solid was added water (0.50 ml). The aqueous solution was extracted with EtOAc (4×0.5 ml). The EtOAc extracts were pooled and the solvent was removed in vacuo to give 5.8 mg (46.5% yield) of a pale yellow oily solid. $^1$H NMR (CD$_3$OD, 400 MHz) d 8.07 (d, J=6.8 Hz, 1H), 7.39 (d, J=7.0 Hz, 1H), 7.30-7.25 (m, 2H), 7.14-7.08 (m, 2H), 6.96 (t, J=7.0 Hz, 1H), 6.36 (s, 1H), 5.56 (s, 1H), 2.28 (s, 3H), 1.69-1.59 (m, 4H). LC/MS (ESI) 310.33/312.25 (M+1/M+3).

Example 9

2-(3-(1-(4-Chlorophenyl)cyclopropyl)-[1,2,4]triazolo[4,3-a]pyridin-8-yl)propane-1,2-diol

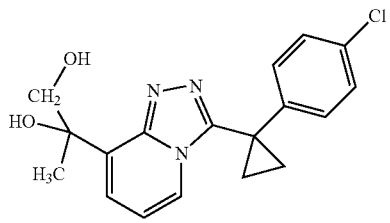 [SMILES: CC(O)(CO)c1cccn2c(C3(c4ccc(Cl)cc4)CC3)nnc12]

To a solution of 3-(1-(4-chlorophenyl)cyclopropyl)-8-(prop-1-en-2-yl)-[1,2,4]triazolo[4,3-a]pyridine (127 mg, 0.410 mmol) in acetone (3.727 ml) and water (0.373 ml) was added 4-methylmorpholine 4-oxide hydrate (117 mg, 0.820 mmol) and 2.5% Osmic acid (0.257 ml, 0.020 mmol) at 0° C. The reaction was allowed to slowly warm to RT and then stirred overnight. The solvent was removed in vacuo to give a residue which was purified by Flash Chromatography using a 12 g Isco column and a gradient from 0/100 (v/v) MeOH/CH$_2$Cl$_2$ to 2.5/97.5 (v/v) MeOH/CH$_2$Cl$_2$. Fractions of 25 ml were collected. Pure fractions were combined and the solvent was removed in vacuo to give 104.1 mg (73.9% yield) of a pale yellow viscous oil. $^1$H NMR (DMSO-d$_6$, 300 MHz) δ 8.05 (dd, J=6.7, 1.2 Hz, 1H), 7.43 (dd, J=6.9, 1.0 Hz, 1H), 7.37-7.30 (m, 2H), 7.15-7.08 (m, 2H), 6.95 (t, J=6.9 Hz, 1H), 4.62 (t, J=6.2, Hz, 1H), 4.10-3.98 (m, 2H), 3.78 (dd, J=10.9, 5.9 Hz, 1H) 1.59 (d, J=11.7 Hz, 7H). LC/MS (ESI) 344.33/346.25 (M+1/M+3).

22
Examples 10a and 10b

[$^{13}$CD$_3$ $^{13}$CD$_2$]3-(1-(4-chlorophenyl)cyclopropyl)-8-(prop-1-en-2-yl)-[1,2,4]triazolo[4,3-a]pyridine and [($^{13}$CD$_3$)$_2$]1-(2-(3-(1-(4-chlorophenyl)cyclopropyl)-[1,2,4]triazolo[4,3-a]pyridin-8-yl)propan-2-yl)pyridin-1-ium chloride

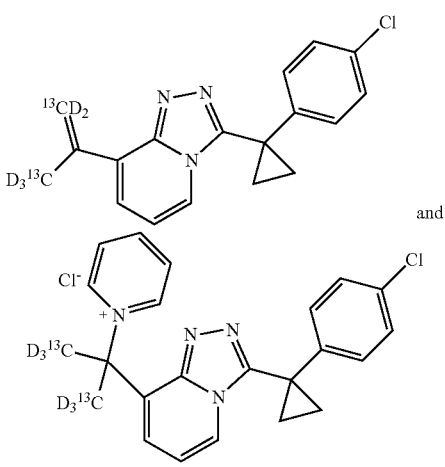

To a round vbottom flask with stirbar was weighed [(OD)($^{13}$CD$_3$)$_2$]2-(3-(1-(4-chlorophenyl)cyclopropyl)-[1,2,4]triazolo[4,3-a]pyridin-8-yl)propan-2-ol (0.5615 g, 1.667 mmol). To this was added pyridine (2.55 ml). The reaction was cooled to 0° C. and phosphorous (V) oxychloride (0.775 ml, 8.33 mmol) was added dropwise over 10 min. The mixture was stirred at 0° C. for 10 min then heated to 60° C. for 40 min. HPLC and LC/MS analysis showed the reaction to be nearly completed. The crude reaction mixture was combined with that of the same from another synthesis of nearly the same scale and was cooled to 0° C. To this was added CH$_2$Cl$_2$ (30 mL) and H$_2$O (7.0 mL) carefully over 15 min. Solid sodium carbonate was carefully added to adjust the pH to ~8 using pH paper. The layers were separated. The aqueous layer was extracted with CH$_2$Cl$_2$ (5×30 mL). The solvent from the combined organic extracts was removed in vacuo to give 1.5582 g of a viscous brown oil. The crude product was purified by Flash Chromatography using an Isco 24 g silica gel column using gradient elution from 0/100 (v/v) MeOH/CH$_2$Cl$_2$ to 3/97 (v/v) MeOH/CH$_2$Cl$_2$ and collecting 28 mL fractions. Fractions 28-32 were pooled and solvent removed in vacuo to give 274 mg of a viscous yellow oil that was a mixture of 30% starting material and 70% desired product as determined by HPLC analysis. Fractions 9-27 were also pooled and the solvent removed in vacuo to give 110.8 mg of a viscous yellow oil that was a mixture of 84% starting material and 16% desired product as determined by HPLC analysis. A more polar product eluted from the column using a gradient starting with 10/90 (v/v) MeOH/CH$_2$Cl$_2$ to 20/80 (v/v) MeOH/CH$_2$Cl$_2$ to give 707.9 mg of a product that was identified as the pyridine adduct salt [($^{13}$CD$_3$)$_2$]1-(2-(3-(1-(4-chlorophenyl)cyclopropyl)-[1,2,4]triazolo[4,3-a]pyridin-8-yl)propan-2-yl)pyridin-1-ium chloride. The 274 mg sample was repurified by Flash Chromatography using an Isco 24 g silica gel column eluting with a gradient from 5/95 (v/v) EtOAc/hexane to 25/75 (v/v) EtOAc/hexane and collecting 28 mL fractions. Fractions containing the product were pooled and solvent removed in vacuo to give 134.7 mg (12.4% yield) of an off white solid. Likewise, the 110.8 mg sample was repurified by Flash Chromatography using an Isco 12 g silica gel column eluting with a gradient from 5/95 (v/v) EtOAc/hexane to 25/75 (v/v) EtOAc/hexane and collecting 20 mL fractions. Fractions containing the product were pooled and solvent removed in vacuo to give 38.9 mg (3.6% yield) of an off white solid. Both desired products had nearly the same NMR and LC/MS spectra. $^1$H NMR (DMSO-$d_6$, 400 MHz) δ 8.06 (d, J=6.2 Hz, 1H), 7.37 (d, J=7.0 Hz, 1H), 7.34-7.29 (m, 2H), 7.08-7.03 (m, 2H), 6.96 (t, J=6.9 Hz, 1H), 1.64-1.53 (m, 4H). LC/MS (ESI) 317.3/319.2 (M+1/M+3). The more polar product that eluted later from the first Flash Chromatography column was identified as [($^{13}$CD$_3$)$_2$]1-(2-(3-(1-(4-chlorophenyl)cyclopropyl)-[1,2,4]triazolo[4,3-a]pyridin-8-yl)propan-2-yl)pyridin-1-ium chloride $^1$H NMR (DMSO-$d_6$, 300 MHz) δ 9.20 (d, J=5.9 Hz, 1H), 8.58 (t, J=7.6 Hz, 1H), 8.28 (s, 1H), 8.08 (t, J=7.2 Hz, 3H), 7.70 (d, J=6.7 Hz, 1H), 7.37-7.26 (m, 2H), 7.22-6.97 (m, 3H), 1.63-1.40 (m, 4H). LC/MS (ESI) 318.3/320.3 (M+1/M+3) from loss of the pyridine to form the stabilized tertiary and benzylic carbocation.

Example 11

[$^{13}$CD$_3$ $^{13}$CD$_2$]3-(1-(4-chlorophenyl)cyclopropyl)-8-(prop-1-en-2-yl)-[1,2,4]triazolo[4,3-a]pyridine

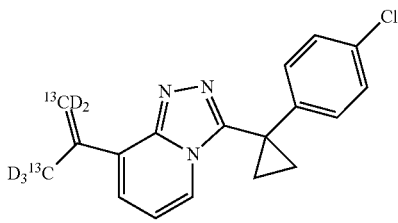

To a 25 mL roundbottom flask was weighed [($^{13}$CD$_3$)$_2$]1-(2-(3-(1-(4-chlorophenyl)cyclopropyl)-[1,2,4]triazolo[4,3-a]pyridin-8-yl)propan-2-yl)pyridin-1-ium chloride (248.6 mg, 0.574 mmol) under a nitrogen To this was syringed DIPEA (0.327 mL, 1.874 mmol) and the mixture was stirred at RT for 30 min. Anhydrous toluene (6.25 mL) was added and the mixture was stirred at 100° C. for 24 h. The reaction mixture was cooled to RT and solvent removed in vacuo. To the crude mixture was added EtOAc (10 mL) and brine (5 mL). The layers were separated. The aqueous layer was extracted with EtOAc (3×10 mL). The solvent from the combined EtOAc extracts was removed in vacuo to obtain 206.4 mg of viscous tan oil. The crude product was combined with that of the same from another reaction at 1.24 times the scale. The combined crude products were purified by Flash Chromatography using a 24 g Isco column and gradient from 20/80 (v/v) EtOAc/hexane to 30/70 (v/v) EtOAc/hexane to give 308.6 mg (75.9% yield) of a colorless oil. $^1$H NMR (CD$_3$OD, 400 MHz) δ 8.08 (d, J=6.8 Hz, 1H), 7.40 (d, J=7.0 Hz, 1H), 7.32-7.26 (m, 2H), 7.15-7.09 (m, 2H), 6.97 (t, J=7.0 Hz, 1H), 1.69-1.61 (m, 4H). LC/MS (ESI) 317.3/319.3 (M+1/M+3).

Example 12

[$^{13}$CD$_3$ $^{13}$CD$_2$]2-(3-(1-(4-chlorophenyl)cyclopropyl)-[1,2,4]triazolo[4,3-a]pyridin-8-yl)propane-1,2-diol

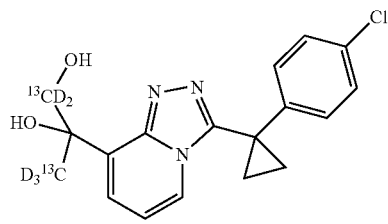

To a solution of [$^{13}$CD$_3$ $^{13}$CD$_2$]3-(1-(4-chlorophenyl)cyclopropyl)-8-(prop-1-en-2-yl)-[1,2,4]triazolo[4,3-a]pyridine (136 mg, 0.429 mmol) in acetone (3.9 mL) and water (0.390 mL) at 0° C. was added 4-methylmorpholine 4-oxide hydrate (122 mg, 0.859 mmol) and 2.5% Osmium tetraoxide (0.267 mL, 0.021 mmol). The reaction was warmed to RT and stirred overnight. The crude reaction mixture was combined with that of the same from another reaction at 1.74 times the scale. The crude reaction was purified by Flash Chromatography using a 24 g Isco silica column and gradient from 0/100 (v/v) MeOH/CH$_2$Cl$_2$ to 2.5/97.5 (v/v) MeOH/CH$_2$Cl$_2$ collecting 25 mL fractions. Pure fractions were combined and the solvent removed in vacuo to give 280.8 mg of a pale yellow viscous oil/glass. This oil/glass was dissolved in CH$_2$Cl$_2$ and the CH$_2$Cl$_2$ was removed in vacuo. This was repeated three additional times to give 268.6 mg (65% yield) of [$^{13}$CD$_3$ $^{13}$CD$_2$]2-(3-(1-(4-chlorophenyl)cyclopropyl)-[1,2,4]triazolo[4,3-a]pyridin-8-yl)propane-1,2-diol as a pale brown foam. $^1$H NMR (CD$_3$OD, 300 MHz) δ 8.06 (d, J=5.9 Hz, 1H), 7.57 (d, J=6.7 Hz, 1H), 7.38-7.22 (m, 2H), 7.18-7.07 (m, 2H), 6.96 (t, J=6.9 Hz, 1H), 1.74-1.53 (m, 4H). LC/MS (ESI) 351.3/353.3 (M+1/M+3)

What is claimed is:

1. A compound, enantiomer, diastereomer, or salt thereof, of a compound of formula I:

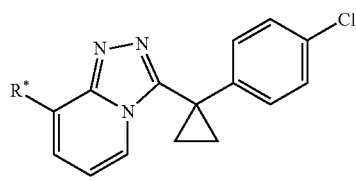

wherein R* is an isotopically labeled hydroxypropyl moiety.

2. The compound, enantiomer, diastereomer, or salt thereof, of claim 1, wherein the compound is a compound of formula Ia, Ib, Ic, Id, Ie, If or Ig:

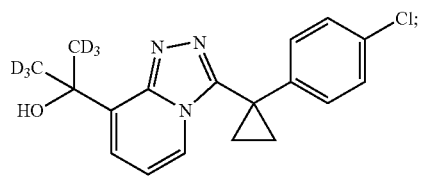

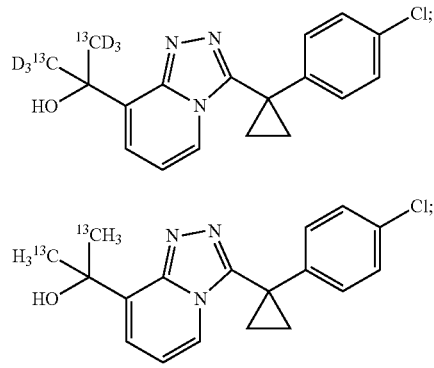

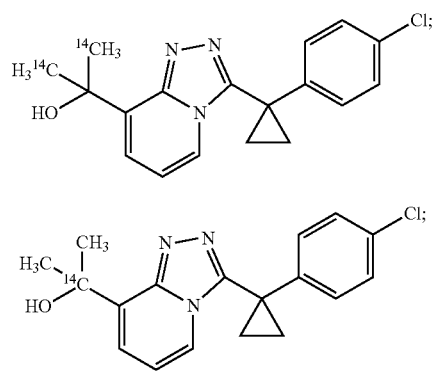

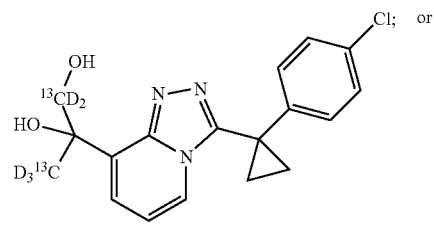

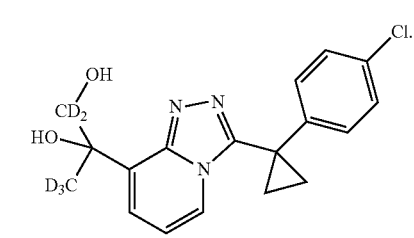

3. The compound, enantiomer, diastereomer, or salt thereof, of claim 1, wherein the compound is a compound of formula Ia:

4. The compound, enantiomer, diastereomer, or salt thereof, of claim 1, wherein the compound is a compound of formula Ib:

5. The compound, enantiomer, diastereomer, or salt thereof, of claim 1, wherein the compound is a compound of formula Ic:

6. The compound, enantiomer, diastereomer, or salt thereof, of claim 1, wherein the compound is a compound of formula Id:

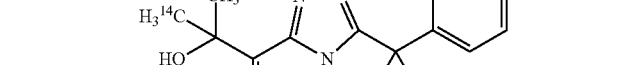

7. The compound, enantiomer, diastereomer, or salt thereof, of claim 1, wherein the compound is a compound of formula Ie:

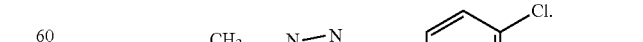

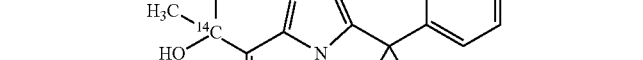

8. A compound, enantiomer, diastereomer, or salt thereof, of claim 1, wherein the compound is a compound of formula If:

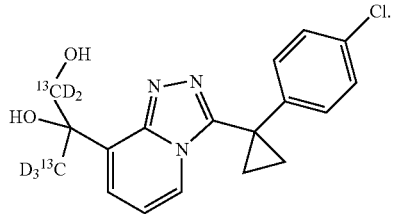

If

9. A compound, enantiomer, diastereomer, or salt thereof, of claim 1, wherein the compound is a compound of formula Ig:

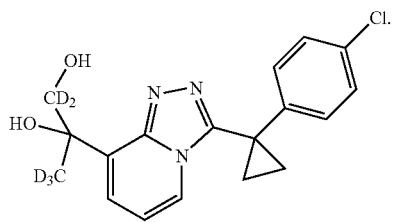

Ig

10. A compound, enantiomer, diastereomer, or salt thereof, of a compound of formula II:

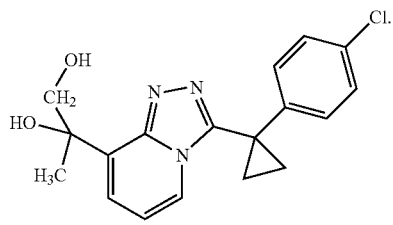

II

11. A pharmaceutical composition comprising a compound of claim 1 and a pharmaceutically acceptable carrier.

12. The pharmaceutical composition of claim 10 further comprising at least one additional therapeutic agent.

13. A method for treating or slowing the progression of diabetes, atherosclerosis, hyperglycemia, obesity, dyslipidemia, hypertension, cognitive impairment, rheumatoid arthritis, osteoarthritis, glaucoma, Cushing's Disease and Metabolic Syndrome, which comprises administering to a mammalian patient in need of treatment a therapeutically effective amount of at least one compound, enantiomers, diastereomers, or salts thereof, of claim 1.

14. A method for treating or slowing the progression of diabetes, which comprises administering to a mammalian patient in need of treatment a therapeutically effective amount of at least one compound, enantiomers, diastereomers, or salts thereof, of claim 1.

15. A method for treating or slowing the progression of atherosclerosis or dyslipidemia, which comprises administering to a mammalian patient in need of treatment a therapeutically effective amount of at least one compound, enantiomers, diastereomers, or salts thereof, of claim 1.

* * * * *